(12) United States Patent
Mayfield

(10) Patent No.: US 7,749,206 B2
(45) Date of Patent: Jul. 6, 2010

(54) CONDOM RETAINING DEVICE

(76) Inventor: Anthony Clay Mayfield, 784 Richard St., Marietta, GA (US) 30060

( * ) Notice: Subject to any disclaimer, the term of this patent is extended or adjusted under 35 U.S.C. 154(b) by 0 days.

(21) Appl. No.: 11/285,262

(22) Filed: Nov. 21, 2005

(65) Prior Publication Data

US 2006/0124135 A1   Jun. 15, 2006

Related U.S. Application Data

(60) Provisional application No. 60/593,157, filed on Dec. 15, 2004.

(51) Int. Cl.
*A61F 5/44* (2006.01)
(52) U.S. Cl. .................. 604/351; 128/844; 128/842; 128/918; 604/346
(58) Field of Classification Search ................ 128/842, 128/844, 918; 604/327, 328, 346, 347, 349, 604/353, 351, 355
See application file for complete search history.

(56) References Cited

U.S. PATENT DOCUMENTS

| | | | | |
|---|---|---|---|---|
| 4,807,611 A | * | 2/1989 | Johnson | 128/844 |
| 4,906,242 A | | 3/1990 | Thomas | |
| 4,942,885 A | * | 7/1990 | Davis et al. | 128/842 |
| 4,966,594 A | | 10/1990 | Thomas | |
| 5,158,556 A | * | 10/1992 | Starley | 604/351 |

* cited by examiner

*Primary Examiner*—Patricia M Bianco
*Assistant Examiner*—Camtu T Nguyen
(74) *Attorney, Agent, or Firm*—Gardner Groff Greenwald & Villanueva, PC; Nigamnarayan Acharya

(57) ABSTRACT

A condom retaining device for use with a male condom in place on a male member having at least one retaining member adapted to fit at least partially around the male member, and a retaining means for securing the at least one retaining member about the user.

3 Claims, 7 Drawing Sheets

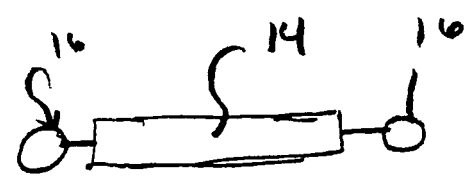
Fig. 6A　　　　　　Fig. 6B
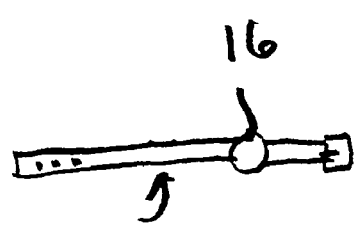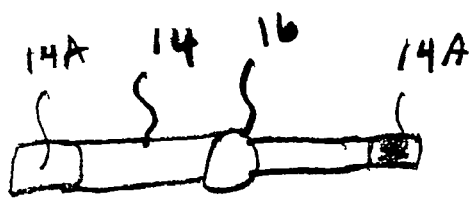
Fig. 6C　　　　　　Fig. 6D

CONDOM RETAINING DEVICE

STATEMENT OF RELATED APPLICATIONS

This application is a Nonprovisional patent application claiming priority on U.S. Provisional Patent Application No. 60/593,157 entitled "Condom Collar" having a filing date of Dec. 15, 2004, which is hereby incorporated by reference.

BACKGROUND OF THE INVENTION

1. Technical Field

This invention relates to condoms and devices for improving the efficacy of condoms. More particularly, this invention relates to a device that enables condom users to more effectively maintain the position of the condom on the male member and/or to prevent the condom from slipping off the male member.

2. Prior Art

Male condom sales have grown dramatically over the past decades and condom use has reached unprecedented acceptance. With the growing attention to AIDS and other sexually transmitted diseases and to unwanted pregnancies, condom sales and use will undoubtedly continue to increase. Specifically, male condoms have been used to prevent pregnancy and the transmission of sexually transmitted diseases by limiting the travel of ejaculate and sperm from a condom wearing male to his partner.

While male condoms are certainly a barrier against diseases and unwanted pregnancies, the effectiveness of condoms can be reduced by any slippage that occurs during the course of sexual activity. Slippage occurs when the worn condom slips off or rolls down to the point that it allows passage of bodily fluids between partners. As condoms can slip off during or following sexual activity, the possibility of infection or unwanted conception remains substantial notwithstanding consistent condom use. One estimate suggests that condoms slip off during sexual activity up to 5% of acts of vaginal intercourse and rolls or slip down up in to 13% of the acts. In cases where the condom slips off or slips down, the possibility of infection or unwanted conception increases dramatically.

Accordingly, there is always a need for devices for improving the efficacy of condoms. There is also a need for such devices to decrease the chances of a condom slipping down or off of the user. Such devices should also help maintain the position of the condom on the user. It is to these needs among others that the present invention is directed.

BRIEF SUMMARY OF THE INVENTION

Briefly, this invention is a condom retaining device for use with a male condom in place on a male member. The condom retaining device has at least one retaining member adapted to fit at least partially around the male member and a retaining means for holding the at least one retaining member about waist of the male. In one embodiment, the condom retaining device comprises a waistband and a retaining member with an opening adapted to fit at least partially around the male member. As will be seen, a condom sheathed male member may pass into opening of the retaining member up until the base of condom flanks the retaining member.

More particularly, the male member with the condom fits into condom retaining device such that the base of the condom is held by the retaining member. By securing the base of the condom with the condom retaining device, it is possible to secure the condom in place on the male member. As will be evident, the internal diameter of the retaining member should be large enough so as to move freely along the male member. However, the tightness of the retaining member should be sufficient to maintain an adequate seal around the base of the male member between the condom and the male member, but not tight enough to restrict blood circulation or cause undue discomfort.

In operation and use, after a male condom is placed on the user, the user, utilizing the elasticity of the waistband, places retaining member over the condom such that the retaining member secures the base of condom. As should be evident, the condom-sheathed male member should pass through the retaining member. After the base of the condom is secured by the retaining member, sexual activity may be initiated. Once any sexual activity is over, the condom retainer, again utilizing the elasticity of the waistband, is passed over the male member and the condom then can be removed and discarded.

One advantage of the condom retainer is that the condom retainer also may improve the quality and duration of the erection and may prevent premature ejaculation. More particularly, as condom retainer has a retaining member that can retain the condom on the male member during coitus and can restrict the flow of blood from the male member, it may be possible that condom retainer can improve the maintenance of the erection by the user. Thus, this invention may be able to both improve the efficacy of condoms and to improve the quality and duration of an erection and prevent premature ejaculation.

These features and other features and advantages of the present invention and the complementary method for installation and use of the invention will become more apparent to those of ordinary skill in the art when the following detailed description of the preferred embodiments is read in conjunction with the appended figures, in which like reference numerals represent like components throughout the various figures.

BRIEF DESCRIPTION OF THE FIGURES

FIGS. 6A-D are additional alternative embodiment of the present invention.

DETAILED DESCRIPTION OF THE PREFERRED EMBODIMENTS

Figure 1:
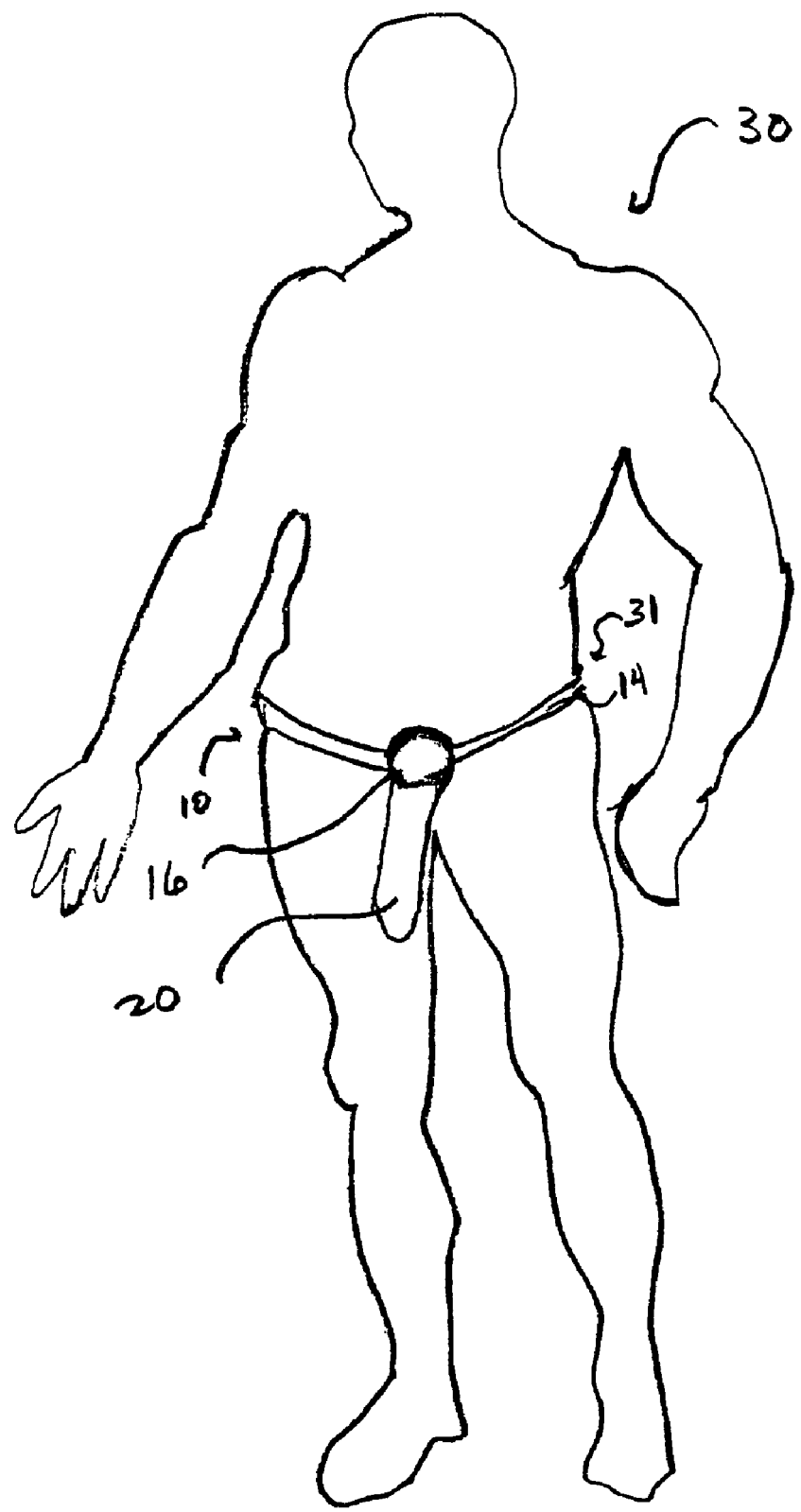
FIG. 1 is a perspective view of a human wearing an illustrative embodiment of the present invention.
Figure 2:
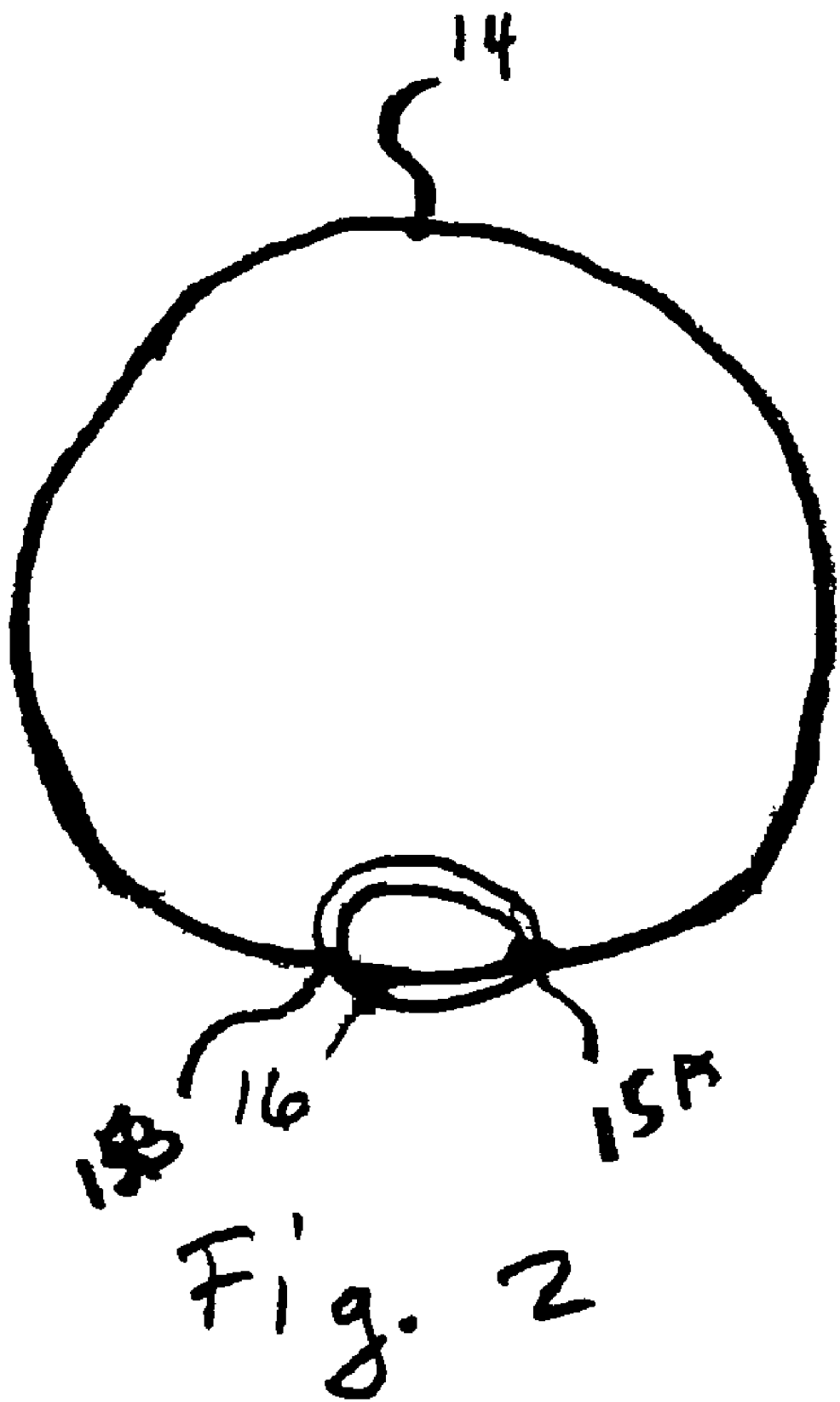
FIG. 2 is a perspective view of a first embodiment of the condom retaining member showing its basic elements shown with a condom ready to be installed.
Figure 3:
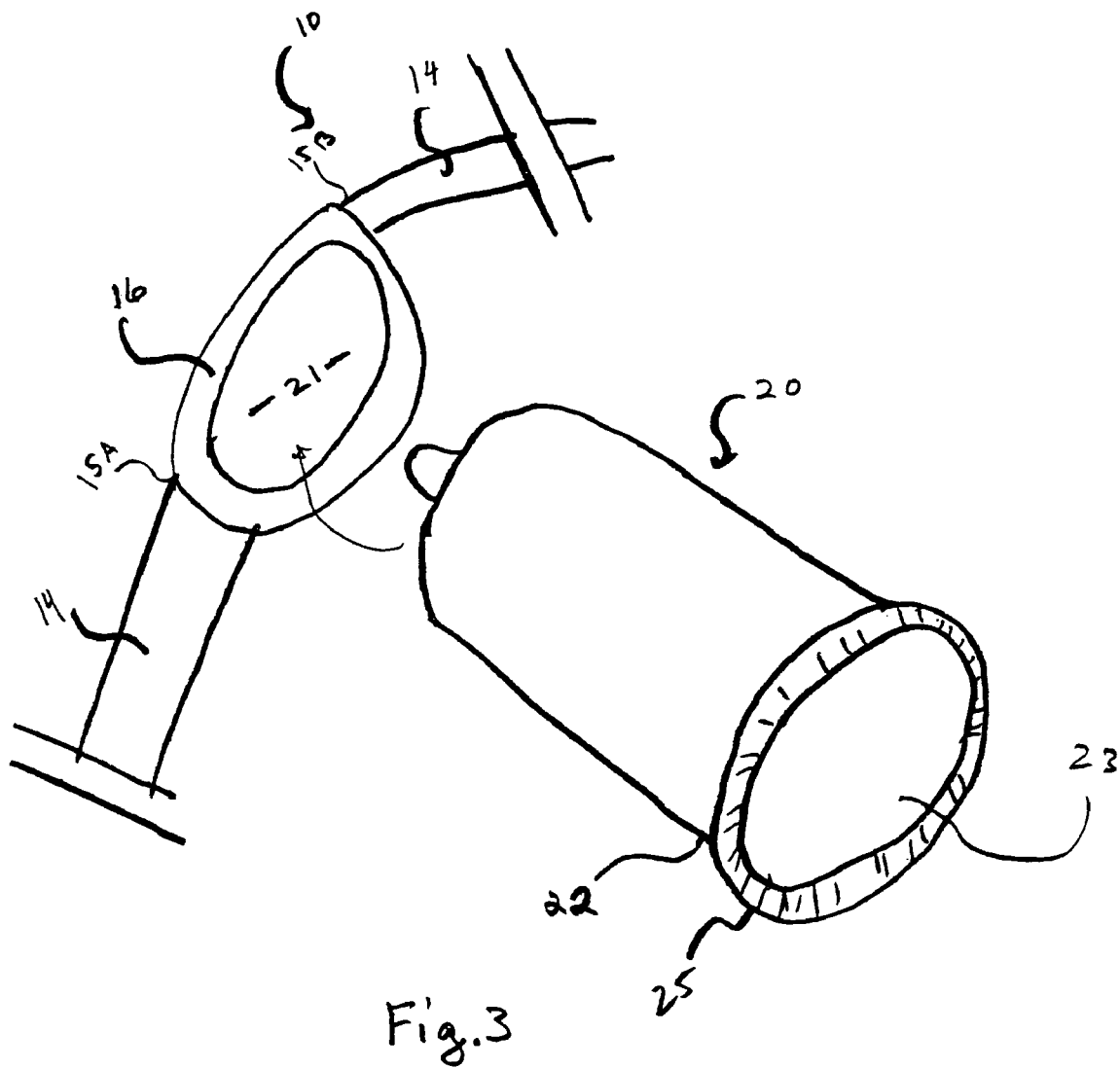
FIG. 3 is a perspective view of the embodiment shown in FIG. 2.
Figure 4:
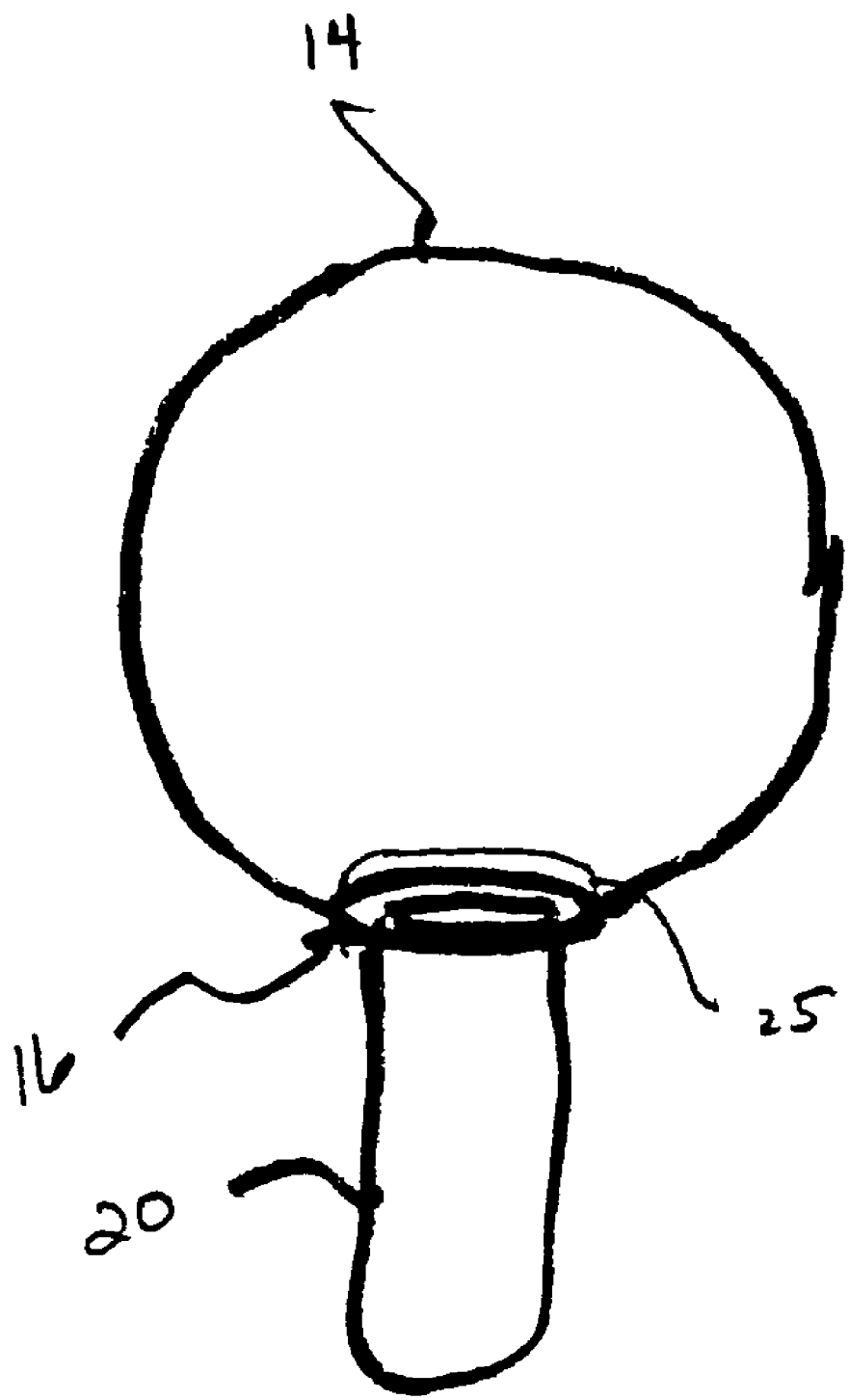
FIG. 4 is a top view of the embodiment shown in FIG. 2 with a condom install therein.
Figure 7:
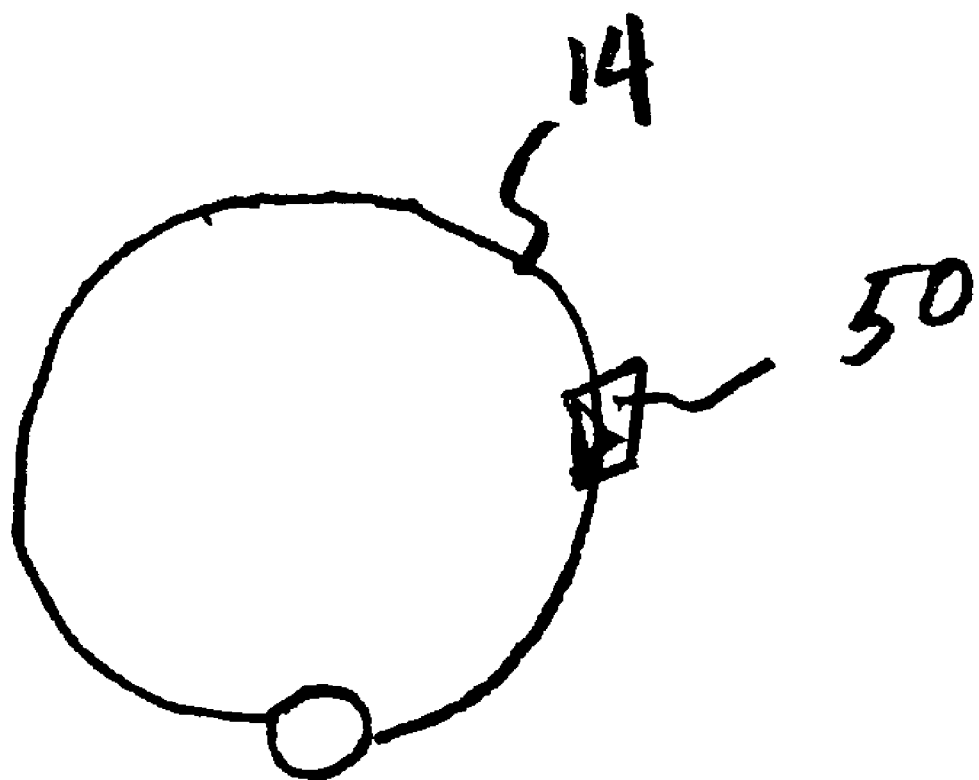
FIG. 7 a perspective view of the embodiment shown in FIG. 1 with a condom package attached to the waistband.

Illustrative embodiments of the present invention shown in FIGS. 1-7 include condom retaining device 10, which when used with conventional male condoms 20, can be used to improve the efficacy of male condoms 20 as a prophylactic measure against sexually transmitted diseases and body fluid transfer. FIG. 1 is perspective view of a human wearing an exemplary condom retaining device 10 with conventional male condom 20. FIG. 2 is perspective view of a first embodiment of the condom retaining device 10 showing its basic elements. FIG. 3 is perspective view of condom retaining device 10 shown in FIG. 2 showing the relationship between the condom retaining member 16 and a conventional male condom 20. FIG. 4 is a top view of condom retaining device 10 showing the relationship between condom retaining device 10 and the base of condom 20. FIGS. 5-6 show alternative embodiments of this invention. FIG. 7 is a perspective view of a packaged condom 20 secured about condom retaining device 10. While the invention is described herein in conjunction with the preferred embodiments, it will be understood that the invention is not limited to these embodiments.

Referring now to FIG. 1, condom retaining device 10 may be used in conjunction with male condom 20 to securely retain condom 20 on the male external genitalia or male member of user 30. As may be seen, condom retaining device 10 minimally comprises at least one retaining member 16 adapted to fit at least partially around the male member and a retaining means 14 for holding the at least one retaining member 16 about the user 30. In a preferred embodiment of the invention, condom retaining device 10 can grasp or hold condom 20 in place on the male member of user 30. Preferably, condom retaining device 10 may be worn snuggly around waist 31 of user 30 without irritating user 30. The efficacy of condom 20 is improved because condom 20 is less likely to slip off or slip down the male member during or after sexual activity.

Referring now to FIG. 2, a first embodiment of condom retaining device 10 comprises waistband 14 and retaining member 16. Ends 15A, 15B of waistband 14 are connected to retaining member 16 in a closed loop. More particularly, waistband 14 has first end 15A attached to retaining member 16 and second end 15B opposite the first end 15A that is likewise attached to the retaining member 16, generally opposite first end 15A. Waistband 14 may be attached to retaining member 16 by glue or stitches. As can be seen, waistband 14 conforms to the curvature of the user's 30 body, while retaining member 16 conforms to the condom-sheathed male member.

Referring now to FIG. 3, condom 20 with a male member (not shown) can pass into opening 21 of retaining member 16 until base 25 of condom 20 flanks retaining member 16. As may be seen, retaining member 16 is dimensioned to allow condom 20 with a male member to pass therethrough. Preferably, opening 21 is of a size, width and/or diameter so at to grip the male member when positioned at base 25 and can provide sufficient pressure on base 25 of condom 20 to maintain the position of condom 20 on the male member. However, opening 21 should not be so large that base 25 can pass through opening 21, as this may not allow condom 20 to be secured adequately by condom retainer 10.

Referring now to FIG. 4, condom 20 with male member (not shown) fits into condom retaining device 10 such that that base 25 of condom 20 is held by retaining member 16. By securing base 25 with condom retaining device 10, it is possible to secure condom 20 in place over the male member. In preferred embodiments, base 25 flanks or abuts retaining member 16. The internal diameter of retaining member 16 should be large enough so the sheathed male member can move freely. However, the tightness of retaining member 16 should be sufficient to maintain an adequate seal around the base of the male member, but not tight enough to restrict blood circulation or cause undue discomfort. Preferably, retaining member 16 is positioned proximal to sheath 22 of condom 20 at the periphery of condom at its open end 23.

In operation and use, user 30 preferably wears condom retaining device 10 such that retaining member 16 corresponds to and cooperates with the male member. In one embodiment, condom 20 is placed on user's 30 member and then user 30, utilizing the preferred elasticity of waistband 14, places retaining member 16 over condom 20 such that retaining member 16 flanks base 25 of condom 20. As should be evident, the condom-sheathed male member should pass through retaining member 16 preferably up to, but at least proximal to, base 25 of condom 20. After base 25 of condom 20 is secured by retaining member 16, condom 20 and the male member should remain in intimate contact. Once any sexual activity is over, condom retaining device 10, again utilizing the elasticity of waistband 14, is passed over the male member. Condom 20 then can be removed from the male member and can be discarded properly.

Figure 5A:
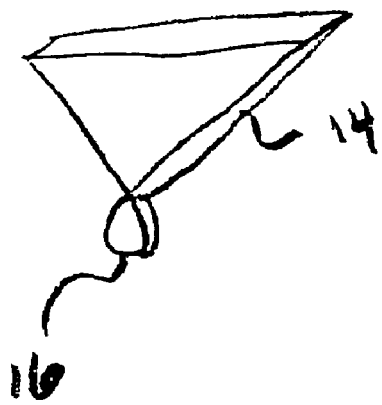
FIGS. 5A-C are alternative embodiment of the present invention.
Figure 5B:
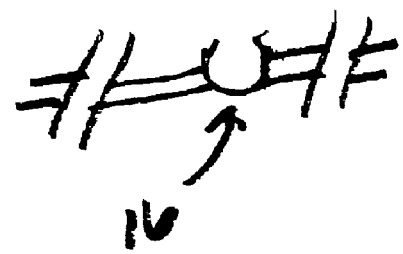
Figure 5C:
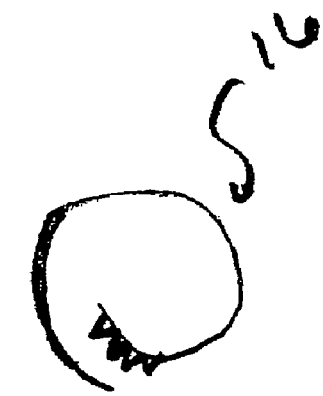

Referring now to FIGS. 5A-B, the structure of retaining member 16 may be of various forms, sizes, shapes, elasticity and materials. For example, FIG. 5A shows retaining member 16 as elastic loop formed by overlapping a section of the waistband 14. For another example, FIG. 5B shows retaining member 16 has a partial loop that can be flipped over or placed about the male member. For another example, FIG. 5C shows retaining member 16 as an adjustable loop that may be adjusted around a male member to form an adequate fit. One of ordinary skill can select the form, shape, size, elasticity and/or other dimensions to accommodate individual differences and comfort levels between users 30.

Referring now to FIGS. 6A-D, waistband 14 may be constructed from in a variety of arrangements. For example, FIGS. 6A-B shows a double yoke assembly in which retaining device 10 is secured by placing waistband 14 around the waist of a male and overlapping retaining members 16 over the male member. FIG. 6B also shows a wider waistband 14 for greater comfort. For another example, FIG. 6C shows waistband 14 as belt-like strap that be adjusted to accommodate various waist sizes. For another example, FIG. 6D shows waistband 14 in which the ends are connected by hook and loop sections 14A. One of ordinary skill can select a suitable waistband for use with the present invention based on the comforts of various users 30.

It understood that that waistband 14 may be of various forms, sizes, shapes, elasticity and materials. It is contemplated that could be made in sizes suitable for various body shapes and sizes. For example, the size of the waistband could be larger to accommodate users 30 with a larger waist. Further, the elasticity of waistband 14 could be reduced for users who prefer less snug fit or less pressured fit. One of ordinary skill can select a suitable waistband for use with the present invention based on the comforts of various users 30.

As may be seen, embodiments of this invention may be constructed using relatively uncomplicated and readily available materials. For example, waistband 14 may be a thread, string, elastic, fabric covered elastic, wire, chain, leather, rubber, or any other attachment means that is attached to retaining member 16 and provides the means for securing retaining member 16 to user 30. Further, the retaining member 16 can be fabricated of materials such as latex, nylon, and preferably polypropylene, which is rigid enough to hold condom 20 without damaging condom 20. Other useful materials which may be used include plastics such as polyurethane, polyvinyl chloride or polyethylene.

Condoms 20 for use with the present invention can include condoms of generally conventional size and shape having an open end 23 and a closed end sheath 22. The cylindrical membrane sheath 22 may be either of the roll-up type or of accordion type construction and is typically made of an elastic material such as latex, polyurethane or other suitable material. In one embodiment shown in FIG. 7, a condom package 50 may be placed on waistband 14 for transportation and access. Preferably, condom 20 is disposable and is removed and discarded in the usual fashion after use.

One advantage of condom retaining 10 is that it also may improve the quality and duration of an erection and prevent premature ejaculation. More particularly, as condom retaining device 10 has retaining member 14 that can retain condom 20 on the male member during coitus and can restrict the flow of blood from the male member, it also may be possible that condom retaining device 10 can improve maintenance of the erection by the user 30. Thus, preferred embodiment may be able to both improve the efficacy of condoms 20 and improve the quality and duration of an erection and prevent premature ejaculation.

The above detailed description of the preferred embodiments, examples, and the appended figures are for illustrative purposes only and are not intended to limit the scope and spirit of the invention, and its equivalents, as defined by the appended claims. One skilled in the art will recognize that many variations can be made to the invention disclosed in this specification without departing from the scope and spirit of the invention.

What is claimed is:

1. A condom retaining device for use with a male condom in place on a male member of a user comprising:
    (a) an annular retaining member that fits circumferentially around the male condom in place on the male member, wherein the retaining member passes over the length of and secures the condom in place on the male member and does not pass over a base of the condom, wherein the retaining member comprises polypropylene, wherein the retaining member contacts the condom base and secures it against the user; and
    (b) a retaining means for securing the retaining member about the user, wherein the annular retaining member is connected directly with the retaining means.

2. The device as claimed in claim 1, wherein the retaining means is a waistband in which each end is connected directly to the retaining member.

3. The condom retaining member as claimed in claim 1, wherein the retaining means is a waistband having two ends; and each end is secured directly to the retaining member.

* * * * *